United States Patent [19]

Magnani

[11] Patent Number: 5,361,632
[45] Date of Patent: Nov. 8, 1994

[54] METHOD AND APPARATUS FOR DETERMINING MULTIPHASE HOLDUP FRACTIONS USING A GRADIOMANOMETER AND A DENSITOMETER

[75] Inventor: Charles F. Magnani, Placentia, Calif.

[73] Assignee: Chevron Research and Technology Company, San Francisco, Calif.

[21] Appl. No.: 874,325

[22] Filed: Apr. 24, 1992

[51] Int. Cl.⁵ .............................................. E21B 49/08
[52] U.S. Cl. ..................................... 73/153; 73/19.10; 73/61.44; 73/155; 166/250; 250/258
[58] Field of Search ............... 73/151, 153, 155, 19.10, 73/19.01, 61.44; 166/250; 250/258, 577

[56] References Cited

U.S. PATENT DOCUMENTS

| | | | |
|---|---|---|---|
| 2,450,265 | 9/1948 | Wolf | 250/258 |
| 3,176,511 | 4/1965 | Widmyer | 73/155 |
| 3,258,963 | 7/1966 | Bryant et al. | 73/155 |
| 3,662,172 | 5/1972 | Youmans | 73/151 |
| 4,056,002 | 11/1977 | Arieh et al. | 73/19.01 |
| 4,342,911 | 8/1982 | French | 250/258 |
| 4,441,361 | 4/1984 | Carlson et al. | 73/155 |
| 4,683,759 | 8/1987 | Skarsvaag et al. | 73/19.10 |
| 4,694,692 | 9/1987 | Brown et al. | 73/155 |
| 4,875,369 | 10/1989 | Delatorre | 73/151 |

OTHER PUBLICATIONS

Courtois et al., "Gamma Sonde Finds Interface in Propane Storage Reservoir," in *Nucleonics,* Jan. 1963, pp. 76 and 78.

*Primary Examiner*—Hezron E. Williams
*Assistant Examiner*—George M. Dombroske
*Attorney, Agent, or Firm*—M. W. Carson; W. K. Turner

[57] ABSTRACT

A method and apparatus determines three phase holdup fractions and flow rates for the individual phases of a fluid flowing in a well. A logging tool comprising a temperature compensated gradiomanometer having a differential pressure detector comprised of two pressure sensors and a nuclear densitometer having a beam source is lowered into a wellbore. The differential pressure between the pressure sensors is measured and an average fluid density is determined. The attenuation of a beam propagating from the beam source through the fluid and to the beam detector is measured, and holdup fractions of the fluid are calculated. Flow rates for the individual phases are determined by adding a flowmeter, and multiplying each holdup fraction by the total flow rate.

12 Claims, 2 Drawing Sheets

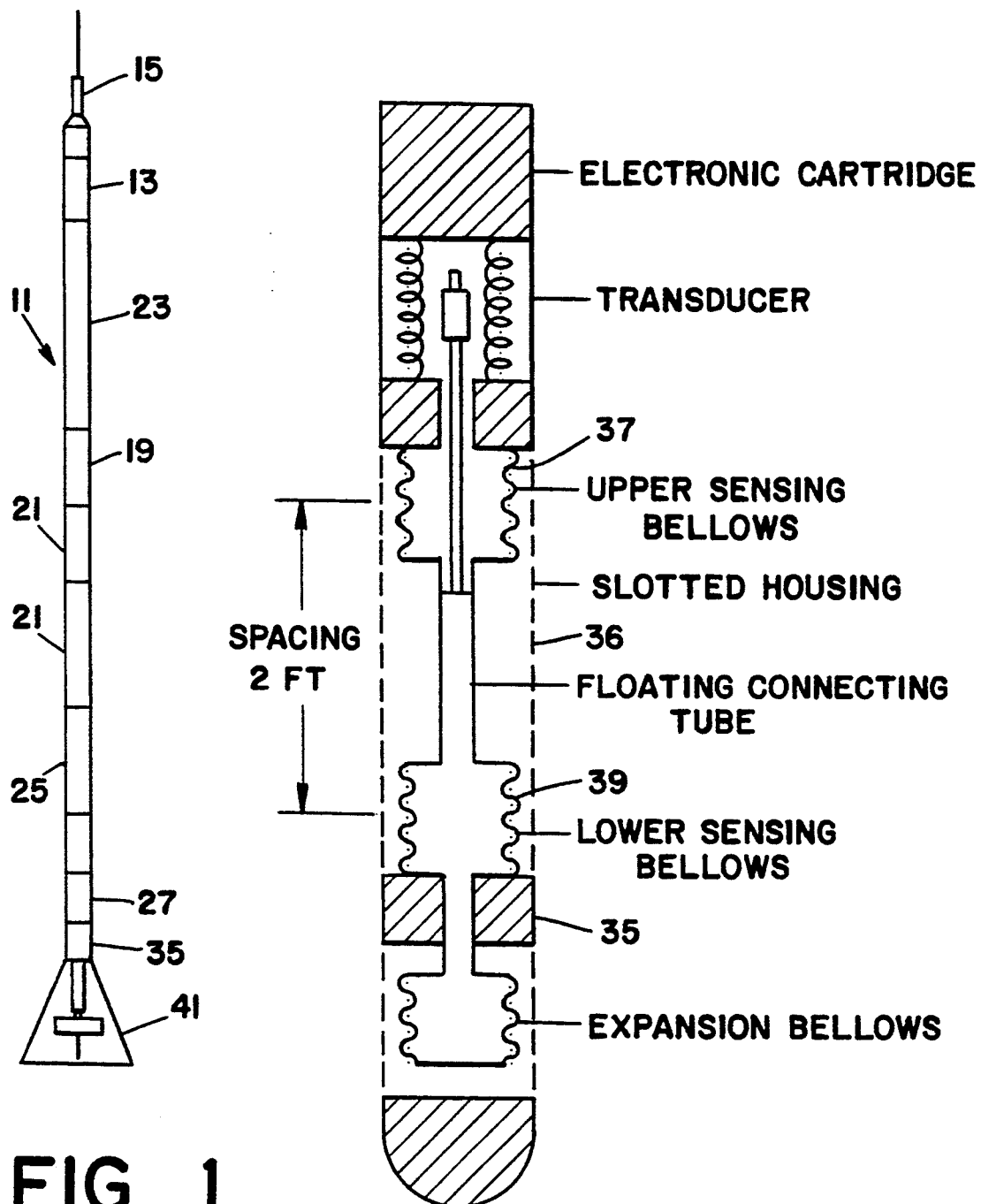

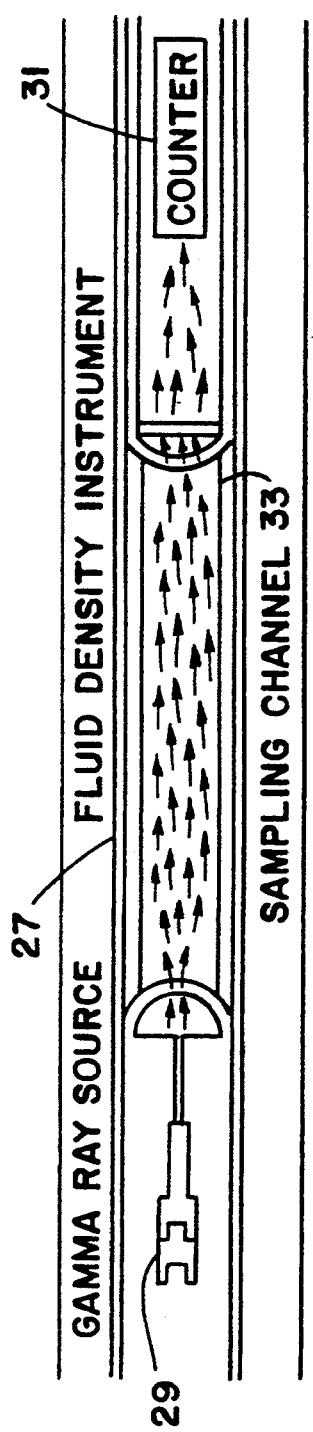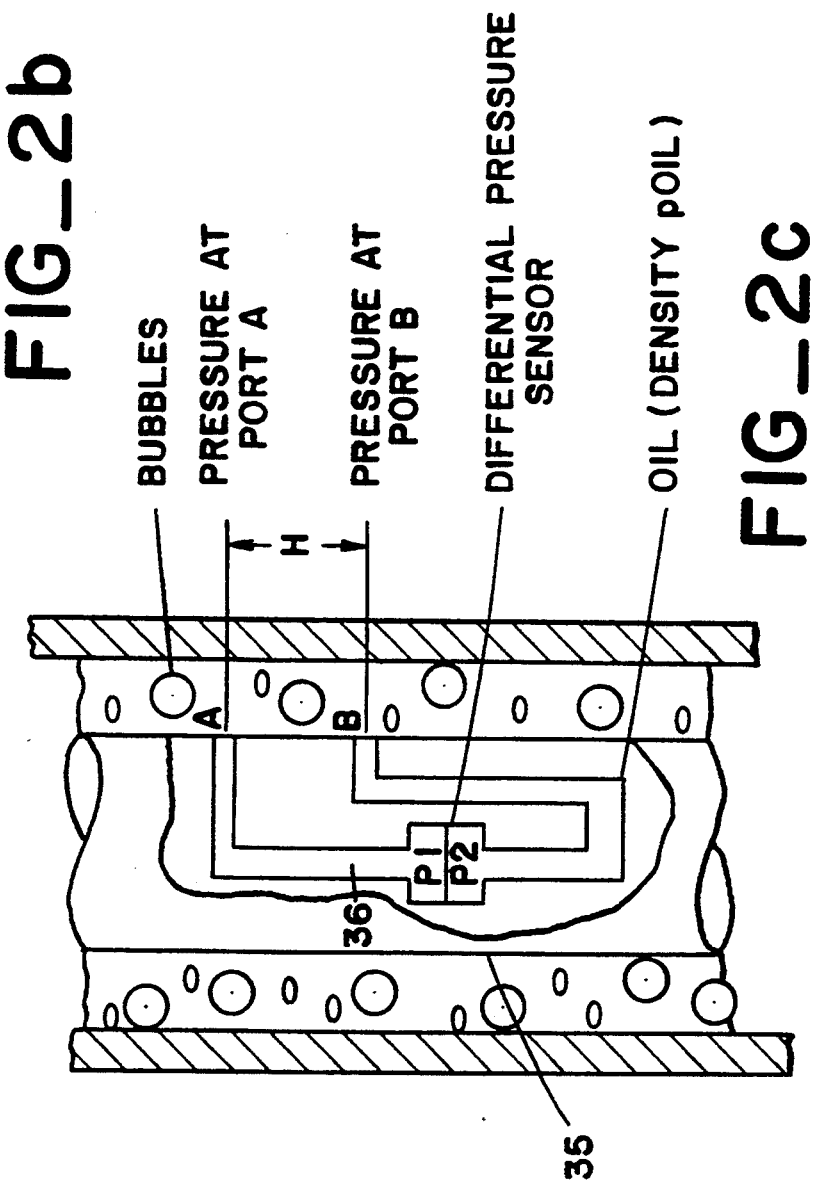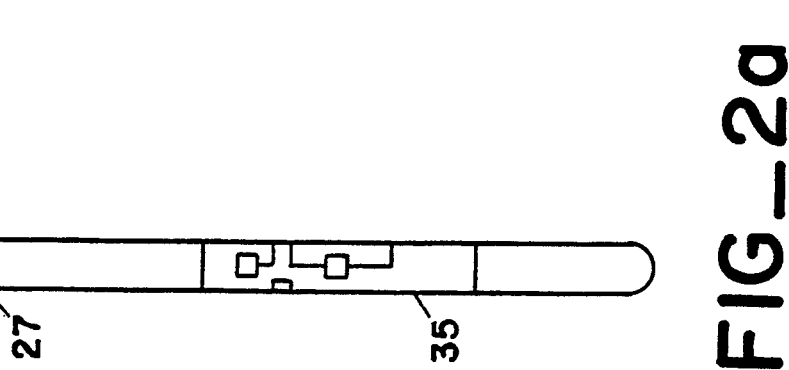

METHOD AND APPARATUS FOR DETERMINING MULTIPHASE HOLDUP FRACTIONS USING A GRADIOMANOMETER AND A DENSITOMETER

FIELD OF THE INVENTION

This invention relates generally to well production logging. More specifically, the present invention provides a method and apparatus for determining multiphase holdup fractions and individual phase flow rates for a fluid flowing in a wellbore, using a gradiomanometer and a densitometer.

BACKGROUND OF THE INVENTION

In the production of oil and gas, it is desirable to determine the fractions of flow through the wellbore that are attributed to oil, water, and gas. Water production often increases as oil reserves are depleted, or from a water injection program. Multiphase production logging is therefore useful to define the production profile and to determine whether a zone is producing oil or whether it is producing large quantities of water.

Current production logging instrumentation is limited by the presence of these multiphase flow regimes. Current multiphase logging techniques require the use of a capacitance probe, along with a gradiomanometer. A gradiomanometer is used to determine the density of the fluid flowing in the wellbore. It measures differential pressure between two membrane-type pressure sensors spaced apart. When pressure drops due to fluid friction and hole deflection are negligible, the gradiomanometer permits direct calculation of the average density of the fluid between the two sensors. Frictional pressure drop and hole deflection are included in the density calculation when warranted. The tool is particularly suited for locating gas entries and standing fluid levels. When oil and water densities are close, the gradiomanometer becomes inaccurate and cannot resolve the subtle differences. The tool is usually ported to sense pressure external to the instrument, thereby sampling a large cross-sectional area of wellbore fluid. This improves overall reliability of the measurement. Gradiomanometer readings must be corrected for well deviation if the well is not vertical.

A capacitance probe responds to the proportion of fluids (holdup) present. The holdup of a phase is the ratio of the volume of that phase to the total volume. For example, if a wellbore has both oil and water in it, and if additional oil is injected at the bottom, some of the water is displaced by the oil bubbles and the oil-water interface will rise. The oil "holds up" the water. The water holdup is the original volume of water prior to oil injection divided by the new volume of water plus the injected oil volume.

The capacitance probe uses the dielectric properties of a fluid to distinguish water from hydrocarbon (oil or gas). The fluid mixture flows between two differently charged surfaces, and the dielectric property of the fluid mixture impedes or permits electron flow between the surfaces. The electron flow is directly related to capacitance and inversely related to frequency. Gaseous hydrocarbons have a dielectric constant very near 1.0, whereas oil has a value close to 2.0. By contrast, the dielectric constant of water is 80. Hence, a good dielectric contrast exists between water and hydrocarbon. Usually, the capacitance probe is scaled directly in water holdup units. Capacitance probe response is linear up to 40 percent water holdup. After 40 percent water holdup, however, the response is nonlinear with poor resolution. Therefore beyond 40 percent water holdup the tool is qualitative at best. In addition, uncertainty exists, as the nonlinear calibration varies among logging companies.

In practice, determining two and three phase flow fractions (holdups) as well as phase fraction flow rates only works when the flow is well-mixed, or homogeneous (bubble flow). Bubble flow occurs when small and discrete bubbles of a lighter phase fluid (oil or gas) travel upward in the column of a continuous heavy phase fluid (water or oil). The bubbles generally move at a higher velocity than the continuous heavy phase. It is rare, however, to observe bubble flow entirely along a producing wellbore. Consequently, measurement errors occur when bubble flow is presumed but does not exist, and therefore, calculated phase rates are imprecise. Other flow regimes which may exist instead include slug flow, froth or transition flow, and/or mist flow.

U.S. Pat. No. 4,520,666, issued to Coblentz et al. discloses a method and apparatus for determining a well's production profile. The method is only used for single phase flow, as opposed to applicant's method and apparatus which determines three phase flow characteristics. This patent uses a temperature log and a spinner flowmeter, instead of measuring fluid density, as applicant does.

U.S. Pat. No. 5,047,632, issued to Hunt, discloses the use of a radioactive tracer to characterize multiphase flow in wells. The present invention does not require tracer injection to determine phase velocity. Instead, applicant determines three phase holdup fractions to determine phase velocity, using a gradiomanometer and a densitometer.

U.S. Pat. No. 4,433,573, issued to Hulin, teaches a method of determining two phase flow rates using a vortex meter and a differential pressure transducer. The present invention measures three phase flow rates and does not require the formation of eddies or vortices.

U.S. Pat. No. 4,856,344, issued to Hunt, discloses the use of a gradiomanometer and a venturi meter to measure two phase flow rate. There is no suggestion of even the need to determine three phase flow characteristics.

U.S. Pat. No. 5,033,288, issued to Castel, teaches a method and device for analyzing a multiphase fluid flowing in a pipe, whereby the fluid is tapped off into a pump and decanted to separate the phases. The respective volumes are determined, and the fluid phases are then analyzed. There is no discussion of the use of a gradiomanometer or a densitometer, or even how the method could work in a wellbore. None of the prior work describes a method for determining three phase holdup fractions of fluids flowing in a wellbore, using a relatively inexpensive and simple device. There is therefore still a need for an improved, accurate technique to determine these holdup fractions.

SUMMARY OF THE INVENTION

A method and apparatus for determining three phase holdup fractions and individual phase flow rates is described. A logging tool comprising a temperature-compensated gradiomanometer having a differential pressure detector comprised of two pressure sensors, and a nuclear densitometer having a gamma ray beam source and a beam detector is lowered to a selected depth in a wellbore. The differential pressure between the pressure sensors is measured, and an average fluid density is determined. The attenuation of a beam propagating from the beam source through the fluid and to the beam detector is measured, and holdup fractions for the fluid are calculated. Flow rates for the individual phases can be determined by adding a means for measuring total flow rate to the logging tool, measuring the total flow rate of the fluid at the selected depth, and multiplying each holdup fraction by the total flow rate.

DESCRIPTION OF THE DRAWINGS

FIG. 1 is a sectional, schematic view of the inventive logging tool.

FIGS. 2a, 2b, and 2c show sectional, schematic views of the inventive logging tool, an enlargement of a nuclear densitometer, and an enlargement of a gradiomanometer, respectively.

FIG. 3 is a schematic sectional view of a gradiomanometer.

DETAILED DESCRIPTION OF THE INVENTION

The proposed invention provides a fast, simple, and inexpensive method and device to determine three phase holdup fractions and individual phase flow rates for a fluid flowing in a wellbore.

A well logging tool is lowered into a wellbore having a fluid flowing therefrom, to a selected depth. Depths are typically selected to be adjacent to a producing geologic formation, or a geologic formation where production type or amount is uncertain. Production logging operations and production logging tools are well known in the well producing art.

Referring to the drawings, FIG. 1 shows a sectional, schematic view of the inventive logging tool 11. Any of several production logging tools known in the art could be modified to construct the inventive logging tool 11. Components common to many existing logging tools include a casing collar locator 13, wireline attachment means 15, a data transmission system telemetry cartridge 17 which controls which signals are being transmitted up and/or downhole at a given time. A quartz pressure gauge 19 and a thermometer (not shown) measure wellbore pressure and temperature, to enable a determination of fluid properties (for oil, water, and gas) at bottomhole conditions. Gamma ray sources 21 and detectors 23 allow correlation of the logging tool's depth with the various geologic formations adjacent to the wellbore. A telemetry interface 25 permits various signals to be transmitted to and from various sensors at a given time.

A novel feature of the inventive logging tool 11 is a nuclear densitometer 27, further illustrated in FIGS. 2a, 2b, and 2c. The nuclear densitometer 27 has a beam source 29 and a beam detector 31. Nuclear densitometers are well known in the art. In the preferred embodiment, the beam is a gamma ray beam.

The nuclear densitometer 27 measures the attenuation of a beam propagating from the beam source 29, through the fluid, and to the beam detector 31. The densitometer 27 diverts the fluid flowing in the wellbore into a chamber 33 which contains the beam source 29 and beam detector The attenuation of the beam is proportional to fluid density. A gamma ray attenuation log is typically scaled in gamma counts per second, with density increasing as the gamma counts decrease. Measured fluid density is usually reported in g/cc using a calibration chart that relates count rate to density. Cesium-137 makes a particularly useful beam source 29. Other potential beam sources include americium-241, cadmium-109, gadolinium-153, cobalt 57, cobalt 60, and barium-133.

The inventive logging tool also has a gradiomanometer 35, as shown in FIGS. 1, 2a, 2c, and 3. The gradiomanometer 35 has a differential pressure detector 36 comprised of two pressure sensors 37 and 39, spaced a known distance apart. As pressure drops due to fluid friction and hole deflection are negligible, direct calculation of an average density of the fluid, between the two pressure sensors from knowing the measured differential pressure between the two pressure sensors at the selected depth is made. Gradiomanometers are well known in the art of production logging. FIG. 2c illustrates a schematic, sectioned view of a typical gradiomanometer. FIG. 3 illustrates a schematic, sectional view of a gradiomanometer provided by Schlumberger Well Services TM. Differential pressure sensors 37 and 39 are bellows, which contract and expand is response to a change of fluid pressure against the logging tool. A temperature-compensated gradiomanometer is especially useful. In deviated wellbores, it is preferable to correct the measured differential pressure for the deviation angle, as buoyant forces tend to segregate the fluids, with lighter phases preferentially flowing in the upper side of the wellbore. For example, clusters of oil bubbles flow faster in a deviated wellbore, and the clusters drag a large amount of water which flows faster than in a vertical well. Use of basket or a diverter type flowmeter are desirable to help homogenize flow and to make gradiomanometer measurements more accurate.

Once the attenuation of the nuclear densitometer beam is measured, the holdup fractions for the fluid at the selected depth can be calculated, using the average density determined from the gradiomanometer.

$$Y_o + Y_\omega + Y_g = 1$$

where $Y_o$ is the holdup fraction of the total cross sectional flow area occupied by oil, $Y_\omega$ is the holdup fraction of the total cross-sectional flow area occupied by water, and $Y_g$ is the holdup fraction of the total cross-sectional flow area occupied by gas.

The amount of measured attenuation of the nuclear densitometer beam, $\mu_m$, is related to the holdup fractions as $$\mu_m = \mu_o Y_o + \mu_\omega Y_\omega + \mu_g Y_g$$

where $\mu_o$, $\mu_\omega$, and $\mu_g$ are the degrees of attenuation attributed to the oil, water, and gas holdup fractions, respectively (also called attenuation coefficients). Measured fluid density from the densitometer, $\rho_m$, can be expressed as $$\rho_m = \rho_o Y_o + \rho_\omega Y_\omega + \rho_g Y_g$$

where $\rho_o$, $\rho_\omega$ and $\rho_g$ are the phase densities attributed to the oil, water, and gas holdup fractions, respectively.

Densitometer beam attenuation $\mu_m$ is related to the difference between initial beam intensity $I_o$ and recorded beam intensity, I (in counts per second).

$$I = I_o e^{-\mu_o Y_o - \mu_\omega Y_\omega - \mu_g Y_g}$$

therefore, $$I = I_o e^{-\mu_o Y_o - \mu_\omega Y_\omega - \mu_g (1 - Y_o - Y_\omega)}$$

therefore $$I = (I_o e^{\mu_g}) e^{-Y_o(\mu_o - \mu_g) - Y_\omega(\mu_\omega - \mu_g)}$$

$$I = I_g e^{-Y_o \mu'_o - Y_\omega \mu'_\omega}$$

where $\mu_o'$ and $\mu_\omega'$ are known from calibration of the densitometer.

$$\mu'_o = \mu_o - \mu_g$$

$$\mu'_\omega = \mu_\omega - \mu_g$$

$$ln(I/I_g) = -Y_o \mu'_o - Y_\omega \mu'_\omega$$

$$ln(I_g/I) = Y_o \mu'_o + Y_\omega \mu'_\omega$$

$\ln(I_g/I)$ can be calculated directly from measurements in the wellbore.

Fluid density is also derived from the gradiomanometer differential pressure measurements.

$$\rho_m = \rho_o Y_o + \rho_\omega Y_\omega + \rho_g Y_g$$

$$\rho_m = \rho_o Y_o + \rho_\omega Y_\omega + \rho_g (1 - Y_o - Y_\omega)$$
$$(\rho_m - \rho_o) = Y_o(\rho_o - \rho_g) + Y_\omega(\rho_\omega - \rho_g)$$

therefore, $$\rho'_m = \rho_m - \rho_g$$

$$\rho'_o = \rho_o - \rho_g$$

$$\rho'_\omega = \rho_\omega - \rho_g$$

$$\rho'_m = Y_o \rho'_o + Y_\omega \rho'_\omega$$

where $\rho'_m$ is the mixture fluid density less the measured gas density from the measured gradiomanometer differential pressure, $\rho'_o$ is the density of the oil phase which is measured less the measured gas density, and $\rho'_\omega$ is the density of the water phase which is measured, less the measured gas density.

Now, the equations that define the holdup fraction from the nuclear densitometer measurements can be combined with the equations that define the holdup fraction from the gradiomanometer measurements. None of the methods existing in the art combine these equations to calculate the holdup fractions for a 3-phase fluid flowing in a wellbore at a selected depth.

From the nuclear densitometer measurements, $$ln (I_g/I) = Y_o \mu'_o + Y_\omega \mu'_\omega$$

From the gradiomanometer measurements, $$\rho'_m = Y_o \rho'_o + Y_\omega \rho'_\omega$$

combining these equations, $$Y_\omega = \frac{\frac{1}{\mu'_o} \ln(I_g/I) - \rho'_m/\rho'_o}{\left( \frac{\mu'_\omega}{\mu'_o} - \frac{\rho'_\omega}{\rho'_o} \right)}$$

-continued $$Y_o = \frac{\frac{\ln(I_g/I)}{\mu'_\omega} - \rho'_m/\rho'_\omega}{\left( \frac{\mu'_o}{\mu'_\omega} - \frac{\rho'_o}{\rho'_\omega} \right)}$$

therefore, $Y_g = 1 - Y_o - Y_\omega$ to provide the holdup fraction for the gas phase.

The inventive method and apparatus therefore enables three phase holdup fractions for a fluid flowing in a wellbore to be determined, by measuring the nuclear densitometer beam attenuation, and then solving for the holdup fractions using the density measurements obtained from the gradiomanometer.

In another embodiment of the invention, the individual phase flow rates for the fluid flowing in the wellbore can be determined. A means for measuring the total fluid flow rate 41 is attached to the logging tool 11, as shown in FIG. 1. Flow meters are well known in the art of production logging. A basket flowmeter is an especially useful flowmeter, although a diverter type flowmeter may also be used.

To better ensure a homogeneous flow regime past all the sensors, it is frequently desirable to place, for example, a means for measuring total flow rate near the bottom of the logging tool, with a gradiomanometer above it, and another flowmeter above the gradiomanometer, and a densitometer above the second flowmeter.

The individual phase flow rates can be determined by multiplying each holdup fraction ($Y_o$, $Y_\omega$, and $Y_g$) by the total flow rate, as measured by the means for measuring total flow rate.

The inventive method and apparatus for determining three phase holdup fractions and individual phase flow rates for a fluid flowing in a wellbore is generally applicable to all multiphase systems, such as in pipeline flow metering.

While a preferred embodiment of the invention has been described and illustrated, it should be apparent that many modifications can be made thereto without departing from the spirit or scope of the invention. Accordingly, the invention is not limited by the foregoing description, but is only limited by the scope of the claims appended hereto.

What is claimed is:

1. A method for determining three phase holdup fractions for a fluid flowing in a wellbore comprising the steps of:
   (a) lowering a logging tool into said wellbore to a selected depth, said logging tool further comprising a gradiomanometer having a differential pressure detector comprising two pressure sensors, and a nuclear densitometer having a beam source and a beam detector;
   (b) measuring the differential pressure between said pressure sensors at said selected depth;
   (c) determining an average density of the fluid, between said pressure sensors, from said measured differential pressure;
   (d) measuring the attenuation of a beam propagating from said beam source through said fluid and to said beam detector at said selected depth; and
   (e) calculating said holdup fractions for said fluid at said selected depth from said average density and said measured attenuation.

2. The method of claim 1 wherein said gradiomanometer is temperature-compensated.

3. The method of claim 1 wherein said measured differential pressure is corrected for wellbore deviation.

4. The method of claim 1 wherein said beam is a gamma ray beam.

5. The method of claim 4 wherein said beam source is Cesium-137.

6. A method for determining individual phase flow rates for a fluid flowing in a wellbore comprising the steps of:
   (a) lowering a logging tool into said wellbore to a selected depth, said logging tool further comprising a gradiomanometer having a differential pressure detector comprising two pressure sensors, a nuclear densitometer having a beam source and a beam detector, and a means for measuring total fluid flow rate;
   (b) measuring the total flow rate of said fluid at said selected depth;
   (c) measuring the differential pressure between said pressure sensors at said selected depth;
   (d) determining an average density of the fluid between said pressure sensors, from said measured differential pressure;
   (e) measuring the attenuation of a beam propagating from said beam source through said fluid and to said beam detector at said selected depth;
   (f) calculating the individual phase holdup fractions for said fluid at said selected depth from said average density; and
   (g) determining the individual phase flow rates by multiplying each holdup fraction by said total flow rate.

7. An apparatus for determining three phase holdup fractions for a fluid flowing in a wellbore comprising a logging tool, said logging tool comprising a gradiomanometer having a differential pressure detector comprised of two pressure sensors, a nuclear densitometer having a beam source and a beam detector means for measuring the differential pressure between said pressure sensors at a selected depth, means for measuring the attenuation of a beam propagating from said beam source through said fluid and to said beam detector at said selected depth, means for determining an average density of the fluid between said pressure sensors from said measured differential pressure, and means for calculating said holdup fractions for said fluid at said selected depth.

8. The apparatus of claim 7 wherein said gradiomanometer is temperature-compensated.

9. The apparatus of claim 7 wherein said measured differential pressure is corrected for wellbore deviation.

10. The apparatus of claim 7 wherein said beam is a gamma ray beam.

11. The apparatus of claim 10 wherein said beam source is Cesium-137.

12. An apparatus for determining individual phase flow rates for a fluid flowing in a wellbore comprising a logging tool, said logging tool comprising a gradiomanometer having a differential pressure detector comprised of two pressure sensors, a nuclear densitometer having a beam source and a beam detector, means for measuring total flow rate of said fluid at said depth, means for measuring the differential pressure between said pressure sensors at a selected depth, means for measuring the attenuation of a beam propagating from said beam source through said fluid and to said beam detector at said selected depth, means for determining an average density of the fluid between said pressure sensors from said measured differential pressure, and means for calculating said holdup fractions for said fluid at said selected depth, and means for determining the individual flow rates by multiplying each holdup fraction by said total flow rate.

* * * * *